United States Patent [19]

Villari

[11] 4,187,860
[45] Feb. 12, 1980

[54] ARTERIAL BLOOD COLLECTION DEVICE
[75] Inventor: Frank K. Villari, Oak Park, Ill.
[73] Assignee: The Kendall Company, Boston, Mass.
[21] Appl. No.: 829,851
[22] Filed: Sep. 1, 1977
[51] Int. Cl.² .............................................. A61B 5/14
[52] U.S. Cl. .................................. 128/763; 128/766; 128/767; 128/771
[58] Field of Search ................. 128/2 C, 2 F, DIG. 5, 128/218 A, 218 P, 218 R, 214 B, 214 D, 226, 213, 215, 216; 222/95, 98, 206, 214, 386; 141/313, 317; 401/153

[56] References Cited
U.S. PATENT DOCUMENTS

| | | | |
|---|---|---|---|
| 2,907,326 | 10/1959 | Gerarde | 128/216 |
| 3,340,869 | 9/1967 | Bane | 128/2 F |
| 3,785,367 | 1/1974 | Fortin & Sims | 128/2 F |
| 3,867,923 | 2/1975 | West | 128/2 F |

Primary Examiner—Robert W. Michell
Assistant Examiner—Jeffrey W. Tayon
Attorney, Agent, or Firm—Powell L. Sprunger

[57] ABSTRACT

A blood collection device comprising, a housing having a retention space and a hollow needle connected to a distal portion of the housing. The device has an expansible collection bag defining a collection chamber communicating with the needle. The bag is movable responsive to arterial blood pressure between a first configuration of reduced dimensions with air substantially removed from the chamber, and a second configuration of extended dimensions with the chamber enlarged to receive blood.

9 Claims, 5 Drawing Figures

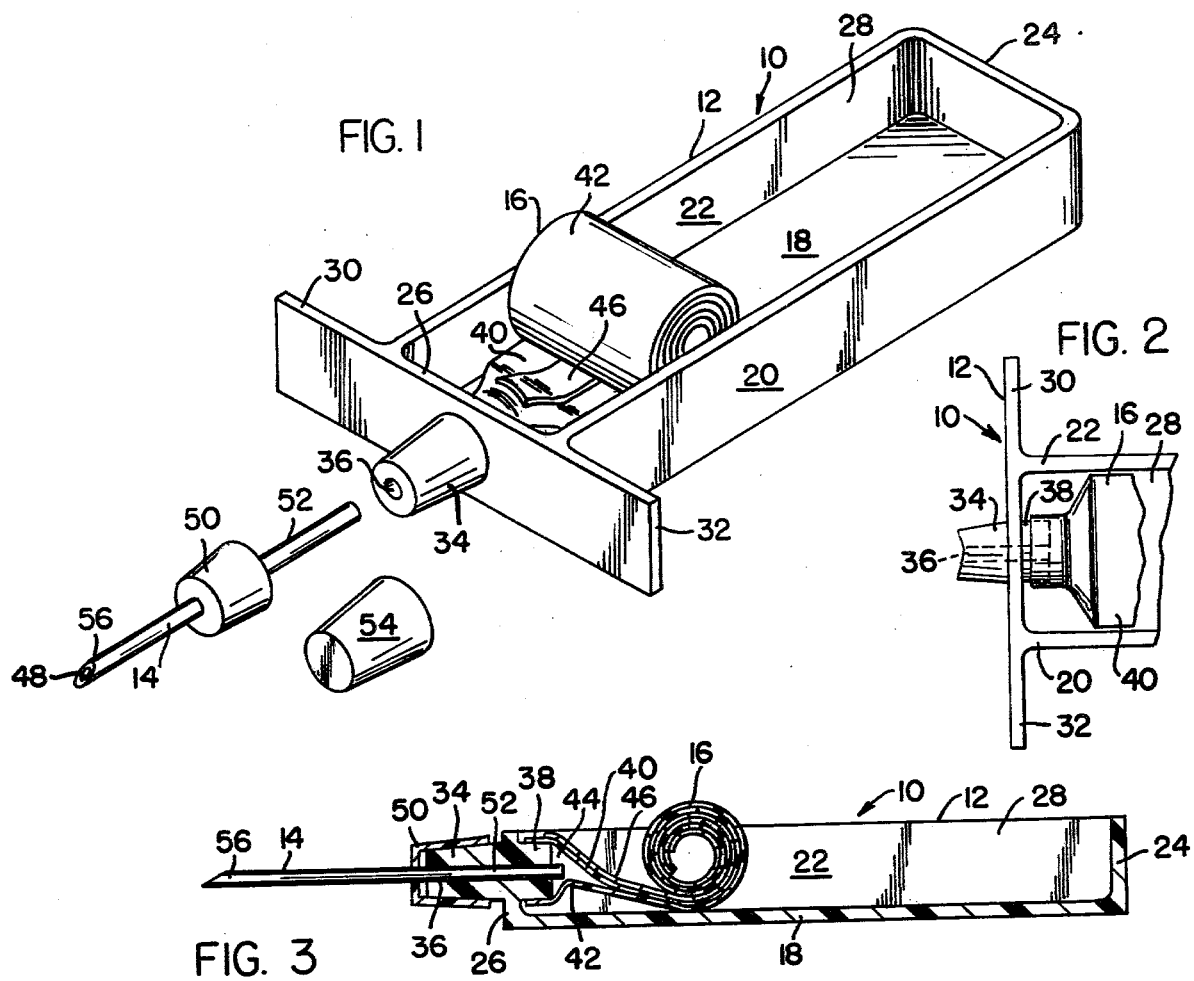
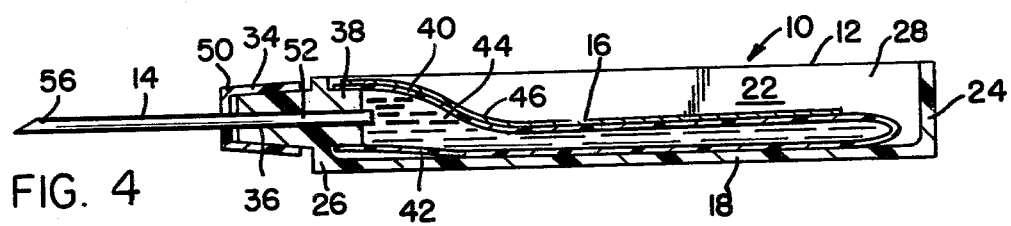
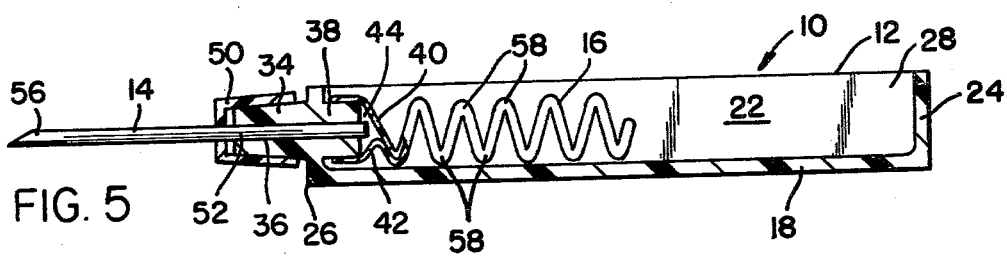

ARTERIAL BLOOD COLLECTION DEVICE

BACKGROUND OF THE INVENTION

The present invention relates to sampling devices, and more particularly to devices for collecting arterial blood.

In recent years, gas analysis of arterial blood has become one of the most important laboratory tests in the management of patients with respiratory and metabolic disorders. However, the collection of a satisfactory arterial blood sample from a patient for analysis has posed a number of difficulties. Initially, in some patients it may be somewhat difficult to ascertain whether the collection device has received arterial or venous blood without measuring for the relatively high arterial pressures during collection. Second, the collection device should minimize contact of the blood sample with air since the air may affect the results of gas analysis. It is also desirable that the sample should not be collected in the presence of a vacuum, since it is believed that the vacuum may modify the gas characteristics of the sample. Finally, the device must prevent coagulation of the blood sample, and should be in a suitable form to permit closure of the sample to air and chilling during the period of time between collection and analysis.

In the past, plastic and glass syringes with a needle have been commonly used to collect the samples. However, the plastic syringes have proven deficient for such purposes due to the relatively high resistance between the syringe plunger and barrel. The plunger resistance in plastic syringes prevents movement of the plunger responsive to arterial pressure alone, and requires that the plunger be manually withdrawn, thus creating an undesirable vacuum in the syringe chamber during collection. Further, since the plungers of plastic syringes are not sufficiently mobile to move under arterial pressure, they do not provide an indication whether arterial or venous blood is being collected. Although the plungers of the glass syringes may be used to detect arterial pressure, the glass syringes are relatively expensive and if the nurse does not exercise sufficient care, the plunger may fall out of the syringe during arterial collection.

SUMMARY OF THE INVENTION

A principal feature of the present invention is the provision of a device of simplified construction for collecting arterial blood in an improved manner.

The collection device of the present invention comprises, a housing having an elongated retention space intermediate opposed ends of the housing, and a hollow needle connected to a distal portion of the housing. The device has an expansible collection bag positioned in the housing space, with the bag having elongated flexible sidewalls defining a collection chamber communicating with the needle. The bag is movable responsive to normal arterial pressure between a first sidewall configuration of reduced bag dimensions, and a second sidewall configuration of extended bag dimensions.

A feature of the present invention is that the bag moves from the first to second configuration to receive arterial blood in the enlarged collection chamber.

Another feature of the invention is that air is substantially removed from the collection chamber in the first bag configuration, and the device thus minimizes the contact of air with the sample.

Yet another feature of the invention is that the bag moves from the first configuration to second configuration responsive to arterial blood pressure, and thus collects the arterial sample in the absence of a vacuum.

Still another feature of the invention is that the bag has sufficient resistance against movement from the first to second configuration to prevent significant extension of the bag under normal venous pressure.

Thus, a feature of the invention is that the device automatically prevents the collection of venous blood which is under a low pressure relative to arterial pressure.

Another feature of the invention is that the bag has an anti-coagulant of blood in the chamber to prevent coagulation of the collected sample.

Still another feature of the invention is that the device may have means for selectively controlling the resistance against movement of the bag from the first to second configuration responsive to pressure in order to permit or prevent collection of venous blood, as desired by the user.

DESCRIPTION OF THE DRAWINGS

In the drawings:

FIG. 1 is a perspective view of the arterial collection device of the present invention;

FIG. 2 is a fragmentary top plan view of the device of FIG. 1;

FIG. 3 is a sectional view of the device of FIG. 1 illustrating a collection bag in a rolled configuration;

FIG. 4 is a sectional view of the device of FIG. 3 illustrating the collection bag in an extended configuration during collection of a sample; and FIG. 5 is an elevational view, taken partly in section, of another embodiment of the collection device of the present invention.

DESCRIPTION OF THE PREFERRED EMBODIMENTS

Referring now to FIGS. 1-3, there is shown an arterial collection device, generally designated 10, having an elongated housing 12, a hollow needle 14 releasably attached to the housing, and an expansible collection bag 16. As shown, the housing 12 has a bottom wall 18, a pair of upstanding sidewalls 20 and 22 at opposed sides of the bottom wall 18, and opposed proximal and distal end walls 24 and 26, respectively, extending between the sidewalls 20 and 22, such that the walls define a cavity 28 to receive the bag 16 with the bottom wall 18 supporting the bag. The housing 12 facilitates handling of the device during collection of a sample, and may have a pair of opposed wings 30 and 32 defining side portions of the distal end wall 26 to further facilitate manipulation of the device. As shown, the housing 12 has a nipple 34 extending from the distal end wall 26, and a passageway 36 extending through the nipple 34 between the housing cavity 28 and the outside of the nipple 34. The housing 12 also has an annular shoulder 38 projecting into the cavity 28 and defining an inner end of the passageway 36.

The collection bag 16 has a pair of opposed first and second elongated sidewalls 40 and 42 having distal ends secured to the housing shoulder 38, and with the sidewalls 40 and 42 defining a closed collection chamber 44 communicating with the housing passageway 36. The sidewalls 40 and 42 may be made of any suitable flexible material impervious to gas diffusion, such as polyethylene or polyvinyl chloride. The bag 16 has an anti-coagulate material 45 of blood, such as heparin, located in the chamber 44. The anti-coagulate material may be placed in the chamber in any suitable form, such as powder, or the chamber walls may be flushed with the material during manufacture of the device. The bag 16 also has an elongated strip 46 of preformed material, such as a suitable heatset plastic, extending longitudinally along the first sidewall 40, such that the strip 46 maintains the bag sidewalls 40 and 42 in a normal rolled configuration of reduced bag dimensions adjacent a distal portion of the cavity 28, as illustrated in FIGS. 1 and 3. In this configuration, air is substantially removed from the bag chamber 44 in order to minimize contact of air with the blood sample when received in the chamber. Further, the strip 46 prevents unrolling of the bag sidewalls below a predetermined blood pressure for a purpose which will be further described below. If desired, the strip 46 may be removably attached to the bag in order to permit removal of the strip and modify the resistance against bag extension responsive to blood pressure. Thus, the strip 46 prevents extension of the bag below a predetermined pressure if not removed from the bag, and may be removed from the bag to permit extension of the bag at relatively low blood pressures, if desired.

With reference to FIGS. 1 and 3, the needle 14 has a tip 56, a lumen 48 extending through the needle, and a hub 50 which may be positioned on the housing nipple 34 in order to releasably attach the needle 14 to the housing with the needle communicating with the bag chamber 44. If desired, the needle 14 may have an inner portion 52 receivable in the housing passageway 36 to facilitate placement of the needle on the housing 12. Further, the device 10 has a cap 54 which may be releasably attached to the housing nipple 34 to close the passageway 36 when the needle 14 is removed from the housing.

In use for collecting an arterial blood sample, the needle 14 is attached to the housing nipple 34, and a puncture of the patient is made with the needle tip 56 while the housing 12 of the device is used for manipulation during the puncture. The strip 46 on the bag 16 prevents extension of the bag below normal arterial pressure, and thus prevents the inadvertent collection of a venous sample at relatively low blood pressures. Once the needle tip 56 is properly located in the artery, the relatively high arterial blood pressure causes flow of the arterial blood through the needle 14 into the bag chamber 44, and the bag sidewalls 40 and 42 begin to unroll against the resistance imposed by the strip 46 as the arterial blood flows into the bag chamber 44. Thus, the bag 16 moves from the first sidewall configuration of reduced bag dimensions, as illustrated in FIG. 3, to a second sidewall configuration of extended bag dimensions, as shown in FIG. 4, with the bag chamber 44 enlarged to receive the arterial blood and with the sidewalls extended in the second configuration.

Thus, the collection bag 16 automatically extends responsive to arterial blood pressure in order to collect the sample, and limits the quantity of arterial blood collected in the chamber 44 when the bag is fully extended. In this manner, the arterial blood sample may be collected without the use of a vacuum and while minimizing the contact of air with the sample, either of which might otherwise modify the results of blood gas analysis. Once the sample has been taken, the needle 14 may be removed from the patient and may be inserted into a suitable object, such as cork, to close the needle lumen and prevent passage of air into the bag chamber, if desired. Alternatively, the needle 14 may be removed from the housing 12, and the cap 54 may be placed on the housing nipple 34 to close the passageway 36. In this form, the bag 16 may be chilled and the device may be forwarded to the laboratory for blood gas analysis.

As previously indicated, the strip 46 prevents extension of the bag under relatively low venous pressures. However, if it should be desired to obtain a venous sample, the strip 46 may be removed from the bag to permit extension of the bag at relatively low venous pressures in order to collect a venous sample.

Another embodiment of the present invention is illustrated in FIG. 5, in which like reference numerals designate like parts. In this embodiment, the bag 16 is laterally folded about a plurality of fold lines 58 in order to define a fan-folded shape of the bag in its first configuration of reduced dimensions. The bag unfolds and expands longitudinally in the cavity 28 responsive to arterial blood pressure to collect a sample, in a manner as previously described. If desired, the rigidity of the bag sidewalls 40 and 42 may be suitably selected to prevent extension of the bag below a predetermined pressure and prevent collection of venous blood samples.

The foregoing detailed description is given for clearness of understanding only, and no unnecessary limitations should be understood therefrom, as modifications will be obvious to those skilled in the art.

I claim:
1. An arterial collection device, comprising:
an elongated housing having a proximal end, a distal portion, an elongated bottom wall having a pair of opposed sides, and a pair of elongated spaced sidewalls extending upwardly from the sides of said bottom wall and having a pair of upper edges, said bottom wall and sidewalls defining an elongated retention space and an elongated opening at the upper edges of said sidewalls;
a hollow needle connected to a distal portion of the housing; and
an elongated longitudinally expansible collection bag supported by said bottom wall in said housing space, said bag having elongated flexible sidewalls defining a collection chamber communicating with said needle, said bag having means to cause said bag to take a first normally rolled sidewall configuration, said bag being movable responsive to normal arterial pressure while guided by said sidewalls in said retention space between said first sidewall configuration of longitudinally reduced bag dimensions with air substantially removed from said chamber, and a second sidewall configuration of longitudinally extended bag dimensions with said chamber enlarged to receive arterial blood and with said bag sidewalls unrolling during movement from said first to second configuration, said means having sufficient resistance against movement from said first to second configurations to prevent significant extension of the bag under normal venous pressure while simultaneously permitting extension of the bag under arterial pressure, and said bag having an anti-coagulate of blood in said chamber.

2. The device of claim 1 including a strip of material extending longitudinally along a bag sidewall, said strip resisting extension of the bag from said first to second configuration.

3. The device of claim 1 including means for releasably attaching the needle to the housing.

4. The device of claim 1 wherein said housing has a nipple at a distal end of the housing, and a passageway extending through the nipple and communicating with the bag chamber, and in which said needle has a hub to releasably attach the needle to the housing nipple.

5. The device of claim 4 including a cap for releasable attachment to the housing nipple for closing said passageway when the needle is removed from the housing.

6. An arterial collection device, comprising:
a housing having walls defining an elongated retention cavity, and a nipple extending from a distal wall of the housing and having a passageway extending through the nipple to said cavity;
a hollow needle having a hub for releasably attaching the needle to the housing nipple; and
an elongated longitudinally expansible collection bag connected to said housing distal wall and positioned in the housing cavity, said bag having a proximal end, a distal end, elongated flexible sidewalls defining a collection chamber communicating with said needle through the passageway, said bag being movable responsive to normal arterial pressure between a first sidewall configuration with said sidewalls being rolled into reduced longitudinal bag dimensions and with air substantially removed from said chamber, and a second sidewall configuration of extended longitudinal bag dimensions with said sidewalls unrolled and said chamber enlarged in the cavity to receive arterial blood, said bag having means providing sufficient resistance against movement from said first to second configurations to prevent significant extension of the bag under normal venous pressure, comprising a strip of material extending longitudinally along the substantial length of one of said sidewalls, with said strip being secured to the bag adjacent the proximal and distal ends thereof, and with said strip biasing said bag from said second to first configurations, and said bag having an anti-coagulate of blood in said chamber.

7. A blood collection device, comprising:
a housing having an elongated retention space intermediate opposed ends of the housing;
a hollow needle connected to a distal portion of the housing;
an expansible collection bag positioned in said housing space, said bag having elongated flexible sidewalls defining a collection chamber communicating with said needle, said bag being movable between a first sidewall configuration of reduced bag dimensions with air substantially removed from said chamber, and a second sidewall configuration of extended bag dimensions with said chamber enlarged to receive blood, said bag having an anti-coagulate of blood in said chamber; and
resilient means contacting the bag for selectively controlling the resistance against movement of said bag from said first to second configuration responsive to pressure between a first amount less than the normal venous pressure and a second amount greater than the normal venous pressure and less than the normal arterial pressure.

8. An arterial collection device, comprising:
an elongated housing having a proximal end, a distal portion, an elongated bottom wall having a pair of opposed sides, and a pair of elongated spaced sidewalls extending upwardly from the sides of said bottom wall and having a pair of upper edges, said bottom wall and sidewalls defining an elongated retention space and an elongated opening at the upper edges of said sidewalls;
a hollow needle connected to a distal portion of the housing; and
an elongated longitudinally expansible collection bag supported by said bottom wall in said housing space, said bag having elongated flexible sidewalls defining a collection chamber communicating with said needle, said bag having means to cause said bag to take a first normally accordion-folded configuration, said bag being movable responsive to normal arterial pressure while guided by said sidewalls in said retention space between said first sidewall configuration of longitudinally reduced bag dimensions with air substantially removed from said chamber, and a second sidewall configuration of longitudinally extended bag dimensions with said chamber enlarged to receive arterial blood and with said sidewalls unfolding during movement from said first to second configuration, said means having sufficient resistance against movement from said first to second configurations to prevent significant extension of the bag under normal venous pressure while simultaneously permitting extension of the bag under arterial pressure, and said bag having an anti-coagulate of blood in said chamber.

9. A blood collection device, comprising:
a housing having an elongated retention space intermediate opposed ends of the housing;
a hollow needle connected to a distal portion of the housing;
an expansible collection bag positioned in said housing space, said bag having elongated flexible sidewalls defining a collection chamber communicating with said needle, said bag being movable between a first sidewall configuration of reduced bag dimensions with air substantially removed from said chamber, and a second sidewall configuration of extended bag dimensions with said chamber enlarged to receive blood, said bag having an anti-coagulate of blood in said chamber; and
means for selectively controlling the resistance against movement of said bag from said first to second configuration responsive to pressure between a first amount less than the normal venous pressure and a second amount greater than the normal venous pressure and less than the normal arterial pressure, said resistance controlling means comprising a removable strip extending longitudinally along a bag sidewall and resisting extension of the bag under pressure in said second amount, said strip being removed from the bag to modify the resistance of the bag under pressure to said first amount.

* * * * *